United States Patent
Chon et al.

(10) Patent No.: US 11,877,955 B2
(45) Date of Patent: Jan. 23, 2024

(54) INFUSION CANNULA

(71) Applicant: Alcon Inc., Fribourg (CH)

(72) Inventors: James Y. Chon, Irvine, CA (US); Robert Jeffrey Heng, Costa Mesa, CA (US); Grace Chuang Liao, Irvine, CA (US); Ashish Sinha, Irvine, CA (US); Satish Yalamanchili, Irvine, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/811,150

(22) Filed: Jul. 7, 2022

(65) Prior Publication Data
US 2023/0026744 A1 Jan. 26, 2023

Related U.S. Application Data

(60) Provisional application No. 63/223,658, filed on Jul. 20, 2021.

(51) Int. Cl.
*A61F 9/007* (2006.01)
*A61M 39/02* (2006.01)
*A61M 39/10* (2006.01)

(52) U.S. Cl.
CPC ..... *A61F 9/00781* (2013.01); *A61M 39/0247* (2013.01); *A61M 39/1011* (2013.01)

(58) Field of Classification Search
CPC .............. A61F 9/00781; A61F 9/0008; A61M 2039/0276; A61M 2039/0279; A61M 39/1055; A61M 39/24; A61M 39/024; A61M 39/1011; A61M 2039/2426; A61B 17/3421
See application file for complete search history.

(56) References Cited

U.S. PATENT DOCUMENTS

| | | | |
|---|---|---|---|
| 3,980,083 A * | 9/1976 | Elliott | A61J 1/2089 604/203 |
| 5,288,290 A | 2/1994 | Brody | |
| 6,551,291 B1 * | 4/2003 | de Juan, Jr | A61F 9/00727 604/289 |
| 7,783,346 B2 | 8/2010 | Smith et al. | |
| 8,251,980 B2 | 8/2012 | Zica | |
| 8,277,418 B2 | 10/2012 | Lopez et al. | |

(Continued)

FOREIGN PATENT DOCUMENTS

| | | | | |
|---|---|---|---|---|
| JP | 2017127410 A * | 7/2017 | ....... | A61B 17/00234 |
| WO | WO-2017094708 A1 * | 6/2017 | ............. | A61F 9/007 |

*Primary Examiner* — Susan S Su
*Assistant Examiner* — Eric Rassavong

(57) ABSTRACT

Embodiments disclosed herein relate to an infusion cannula for infusion/venting of fluids to/from the eye to control intraocular pressure. The infusion cannula includes a tubular body with a tubular inlet located at a proximal end of the tubular body and a tubular outlet located at a distal end of the tubular body. The tubular outlet is aligned with a first longitudinal axis and configured to extend through a septum of a valved cannula hub. The infusion cannula includes a retention piece extending from or coupled to the tubular body. The retention piece has an annular body surrounding the tubular body at the distal end of the tubular body and configured to be coupled to the valved cannula hub. An inner surface of the annular body has a profile configured to form a snap fit with an overhang formed along an outer surface of the valved cannula hub.

14 Claims, 7 Drawing Sheets

(56) References Cited

U.S. PATENT DOCUMENTS

| | | |
|---|---|---|
| 8,343,106 B2 | 1/2013 | Alcon |
| 9,795,508 B2 | 10/2017 | Lopez |
| 9,839,749 B2 | 12/2017 | Johnson |
| 10,610,408 B2 | 4/2020 | Farley |
| 10,905,462 B2 | 2/2021 | Ochoa |
| 11,166,843 B2 | 11/2021 | Hallen |
| 11,173,008 B2 | 11/2021 | Mirsepassi et al. |
| 11,395,713 B2 | 7/2022 | Grueebler et al. |
| 2002/0042605 A1* | 4/2002 | Castaneda .......... A61B 17/3417 606/1 |
| 2003/0208165 A1* | 11/2003 | Christensen .......... A61M 39/26 264/494 |
| 2005/0187524 A1* | 8/2005 | Willis .................. A61M 39/26 604/256 |
| 2006/0089526 A1* | 4/2006 | Chen .................. A61B 1/00142 600/101 |
| 2007/0016137 A1 | 1/2007 | Attinger |
| 2007/0225648 A1* | 9/2007 | Winsor ................ A61M 39/10 604/905 |
| 2008/0033462 A1* | 2/2008 | Di Nardo .......... A61M 39/0247 606/166 |
| 2008/0172009 A1 | 7/2008 | Attinger |
| 2008/0177239 A1 | 7/2008 | Li |
| 2008/0312662 A1 | 12/2008 | Hickingbotham |
| 2009/0076463 A1 | 3/2009 | Attinger |
| 2009/0112166 A1* | 4/2009 | Fangrow, Jr. .......... A61M 5/158 604/167.02 |
| 2009/0232586 A1* | 9/2009 | Diodati .................. F16L 37/32 403/14 |
| 2009/0234292 A1* | 9/2009 | Di Nardo .......... A61B 17/3462 604/167.01 |
| 2010/0036328 A1* | 2/2010 | Dikeman .............. A61M 39/24 604/247 |
| 2011/0130722 A1* | 6/2011 | Fangrow, Jr. .......... A61M 5/158 604/174 |
| 2014/0275923 A1* | 9/2014 | Haffner .................. A61B 5/002 600/377 |
| 2016/0067083 A1* | 3/2016 | Lue ...................... A61F 9/0017 606/107 |
| 2019/0239979 A1 | 8/2019 | Abt |
| 2019/0307527 A1 | 10/2019 | Grueebler |
| 2019/0374248 A1 | 12/2019 | Grueebler |
| 2020/0337901 A1* | 10/2020 | Charles .............. A61F 9/00781 |
| 2022/0233352 A1* | 7/2022 | Peterson ............ A61B 17/3421 |

* cited by examiner

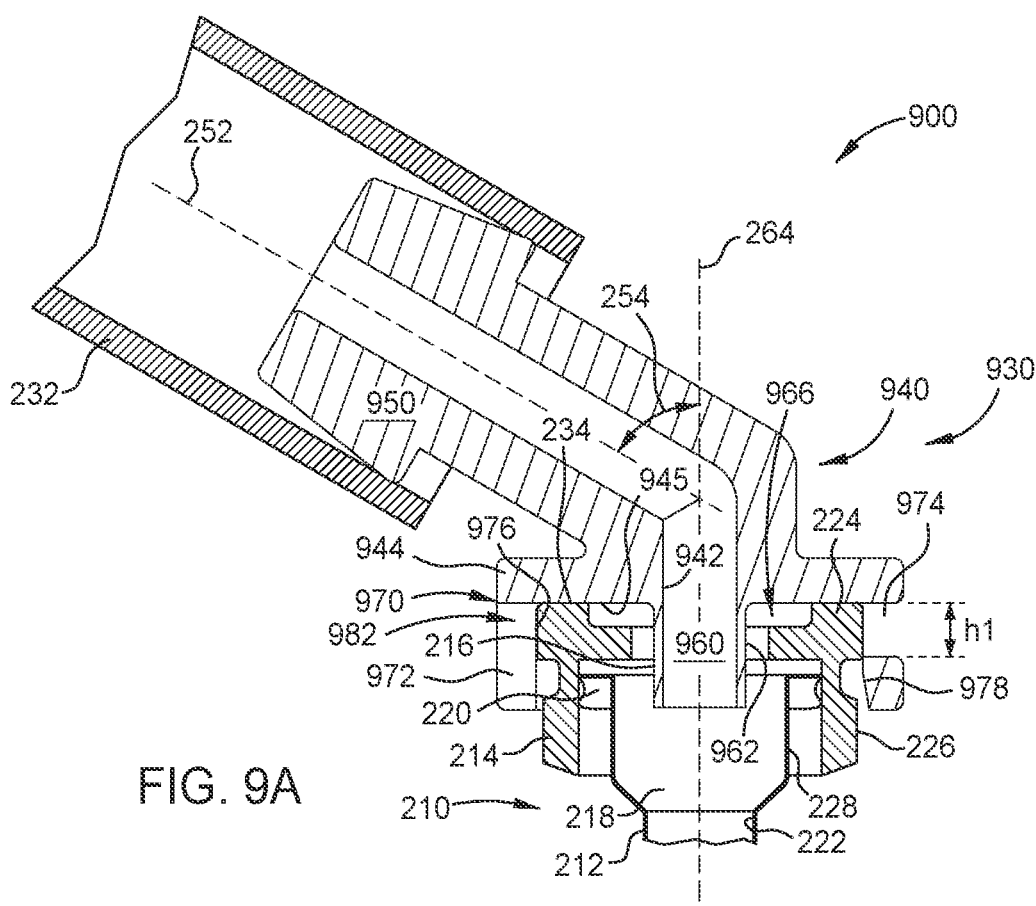
FIG. 9A
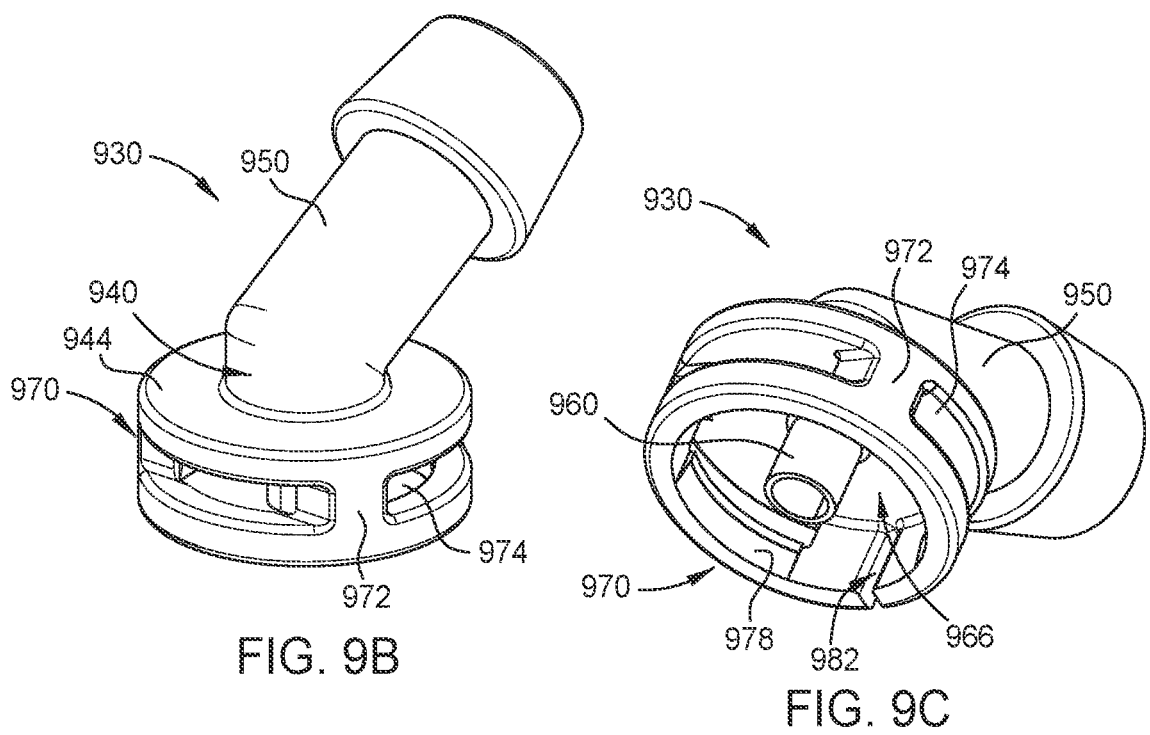
FIG. 9B
FIG. 9C

INFUSION CANNULA

PRIORITY CLAIM

This application claims the benefit of priority of U.S. Provisional Patent Application Ser. No. 63/223,658 titled "INFUSION CANNULA," filed on Jul. 20, 2021, whose inventors are James Y. Chon, Robert Jeffrey Heng, Grace Chuang Liao, Ashish Sinha and Satish Yalamanchili, which is hereby incorporated by reference in its entirety as though fully and completely set forth herein.

TECHNICAL FIELD

The present disclosure relates generally to devices, systems, and methods to control intraocular pressure (IOP) during ophthalmic surgery. More particularly, the present disclosure relates to an infusion cannula and methods of use thereof, which are useful for infusion/venting of fluids to/from the eye.

BACKGROUND

Posterior segment surgical procedures are performed to treat conditions of the back of the eye, such as age-related macular degeneration (AMD), diabetic retinopathy and diabetic vitreous hemorrhage, macular hole, retinal detachment, epiretinal membrane, cytomegalovirus (CMV) retinitis, and others.

Certain problems affecting the back of the eye may require a vitrectomy, or surgical removal of the vitreous, which is a normally clear, gel-like substance that fills the center of the eye helping to provide form and shape to the eye. For example, a vitrectomy may be performed to clear blood and debris from the eye, to remove scar tissue, or to alleviate traction on the retina. FIG. 1A is front schematic view of an eye 100 during an exemplary ophthalmic procedure, such as a vitrectomy. During the procedure shown in FIG. 1A, three separate incisions are made in the pars plana of the eye 100, which is located just behind the iris but in front of the retina. The incisions are used to pass instruments into the eye 100 such as a light pipe, an infusion port, and a vitrectomy cutting device. As shown in FIG. 1A, a valved cannula 110 is positioned with each incision to enable instrument access while, at the same time, providing a self-sealing valve to passively control fluid and pressure communication from inside and outside the eye 100. An exemplary valved cannula 110 is shown in the top isometric view of FIG. 1B. The valved cannula 110 includes a cannula portion 112 having a distal end extending into the eye 100 (shown inside the dashed line on the right side of FIG. 1B) and a hub 114 coupled to a proximal end of the cannula portion 112 and disposed outside the eye 100 and in contact with the front of the eye 100 (shown on the left side of FIG. 1B outside the dashed line and also in FIG. 1A). Note that, as described herein, a distal end or portion of a component refers to the end or the portion that is closer to a patient's body during use thereof. On the other hand, a proximal end or portion of the component refers to the end or the portion that is distanced further away from the patient's body. The valve septum 116 is disposed in alignment with a throughbore 118 (shown in phantom) of the valved cannula 110 for regulating fluid and pressure communication to and from the eye 100.

As vitreous fluid is aspirated during posterior segment surgery, intraocular pressure (IOP) decreases and the eye tends to soften. An infusion cannula may be used, for example in conjunction with one of the valved cannulas 110 of FIG. 1A, to infuse fluid, such as liquid or gas (e.g., balanced salt solution (BSS)), to the eye to maintain IOP and avoid globe deformation or collapse. In addition, maintaining IOP may help maintain scleral rigidity to facilitate movement of the eye and exchange of instruments during the procedure. However, IOP must be carefully regulated, as prolonged periods of elevated IOP can damage eye structures. If IOP becomes too high, another infusion cannula may be used, for example in conjunction with another one of the valved cannulas 110 of FIG. 1A, to vent fluid from the eye to relieve pressure.

Existing infusion cannulas have significant drawbacks. For example, when routing current infusion cannula tubing, tape is used to create a service loop which creates an obstruction and adds an additional procedure step. In addition, existing infusion cannulas couple to the inner surface of the hub which means that existing infusion cannulas are size-specific. Therefore, each different infusion cannula only fits one-size of valved cannula. Furthermore, existing infusion cannulas have an inner diameter which restricts fluid flow compared to a compatible valved cannula, therefore requiring a high pressure to maintain a given fluid flow rate.

Therefore, there is a need for improved devices, systems, and methods for controlling intraocular pressure, and there is a particular need for improved infusion cannulas that address at least some of the drawbacks described above.

BRIEF SUMMARY

The present disclosure relates generally to devices, systems, and methods to control intraocular pressure during ophthalmic surgery, such as posterior segment surgical procedures including vitrectomy. More particularly, the present disclosure relates to an infusion cannula and methods of use thereof, which are useful for infusion/venting of fluids to/from the eye.

Certain embodiments described herein provide an infusion cannula for infusion/venting of fluids to/from the eye to control intraocular pressure. An infusion cannula includes a tubular body with a tubular inlet located at a proximal end of the tubular body and a tubular outlet located at a distal end of the tubular body. The tubular outlet is aligned with a first longitudinal axis and configured to extend through a septum of a valved cannula hub. The infusion cannula includes a retention piece extending from or coupled to the tubular body. The retention piece has an annular body surrounding the tubular body at the distal end of the tubular body and configured to be coupled to the valved cannula hub. An inner surface of the annular body has a profile configured to form a snap fit with an overhang formed along an outer surface of the valved cannula hub.

The following description and the related drawings set forth in detail certain illustrative features of one or more embodiments.

BRIEF DESCRIPTION OF THE DRAWINGS

The appended figures depict certain aspects of one or more disclosed embodiments and are therefore not to be considered limiting of the scope of this disclosure.

FIG. 2A is a side cross-sectional view of a valved cannula assembly including an exemplary infusion cannula assembled with an exemplary valved cannula, in accordance with certain embodiments of the present disclosure.

FIG. 9A is a side cross-sectional view of yet another exemplary infusion cannula shown assembled with the valved cannula of FIG. 2A.

FIG. 9B is a top isometric view of the exemplary infusion cannula of FIG. 9A.

FIG. 9C is a bottom isometric view of the exemplary infusion cannula of FIG. 9A.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments disclosed herein provide devices, systems, and methods to control intraocular pressure (IOP). For example, the disclosed devices, systems, and methods are useful for controlling IOP during ophthalmic surgery, such as posterior segment surgical procedures including vitrectomy. More particularly, embodiments disclose infusion cannulas and methods of use thereof, which are useful for infusion/venting of fluids to/from the eye when assembled with a valved cannula as described in more detail below.

Certain embodiments provide an improved infusion cannula having an angled inlet which helps with routing of inlet tubing to remove the need for creating a service loop. The angled inlet reduces visual and physical obstructions and reduces surgical time by removing a procedure step as described in more detail below. The angled inlet also limits undesirable kinking of the inlet tube which interferes with flow and pressure communication therethrough as described in more detail below. Certain embodiments provide an improved infusion cannula which is configured to be coupled to an outer surface of a valved cannula hub. Coupling of the infusion cannula to the outer surface of the hub enables the infusion cannula to be cross-compatible with different-sized valved cannulas thereby expanding potential use cases for the infusion cannula as described in more detail below. Certain embodiments provide an improved infusion cannula which has an inner diameter for fluid flow which is greater than a corresponding inner diameter of a compatible valved cannula hub. In such embodiments, the improved infusion cannula is configured to reduce overall flow resistance and pressure drop through the infusion cannula which lowers the pressure needed to maintain a given fluid flow rate or, stated another way, increases flow rate at a given source pressure as described in more detail below.

Figure 1A:
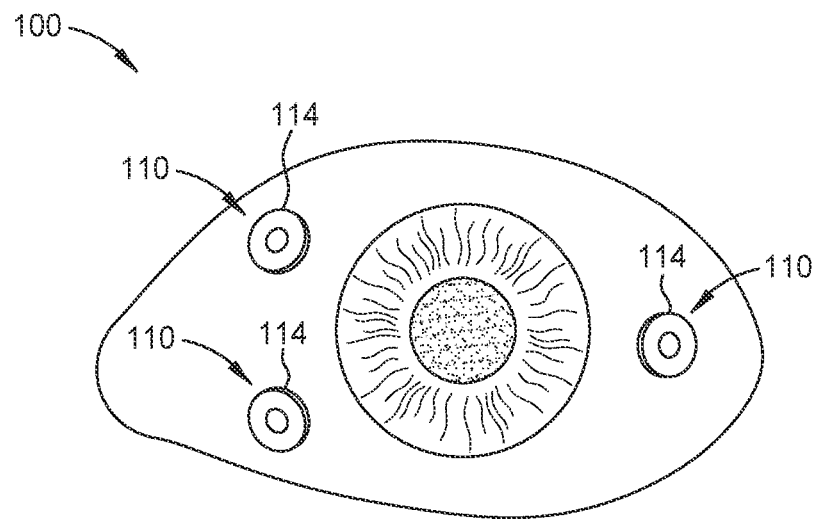
FIG. 1A is front schematic view of an eye during an exemplary ophthalmic procedure.
Figure 1B:
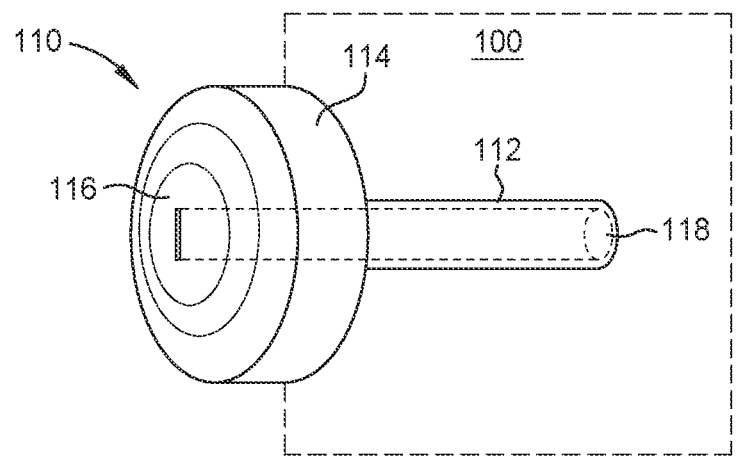
FIG. 1B is a top isometric view of an exemplary valved cannula which may be used during the procedure shown in FIG. 1A.

FIG. 2A is a side cross-sectional view of a valved cannula assembly 200. The valved cannula assembly 200 generally includes a valved cannula 210 having a hub 214 which is coupled to a distal end of an exemplary infusion cannula 230. In certain embodiments, the valved cannula 210 may be constructed and arranged similar to the valved cannula 110 of FIG. 1B, and aspects of the description thereof may be incorporated herein without limitation. As shown in FIG. 2A, a proximal end 228 of the cannula portion 212 of the valved cannula 210 is disposed inside the hub 214. In certain embodiments, to couple the cannula portion 212 to the hub 214, one or more wings 220 extending radially outward from the proximal end 228 of the cannula portion 212 are disposed through corresponding windows formed in the hub 214. In certain embodiments, the valve septum 216 comprises an elastomer material coupled to the proximal end 228 of the cannula portion 212 and having a slit formed therein (shown in FIG. 1B) which is configured to form an air- and water-tight seal with or without an instrument inserted therethrough. The valve septum 216 enables instrument access to the eye via throughbore 218 while, at the same time, sealing the throughbore 218 to regulate fluid and pressure communication from inside and outside the eye. In certain embodiments, valved cannula sizing is specified according to the dimensions of inner diameter 222 such as including 23 Gauge, 25 Gauge, and 27 Gauge valved cannulas, among others.

Figure 2B:
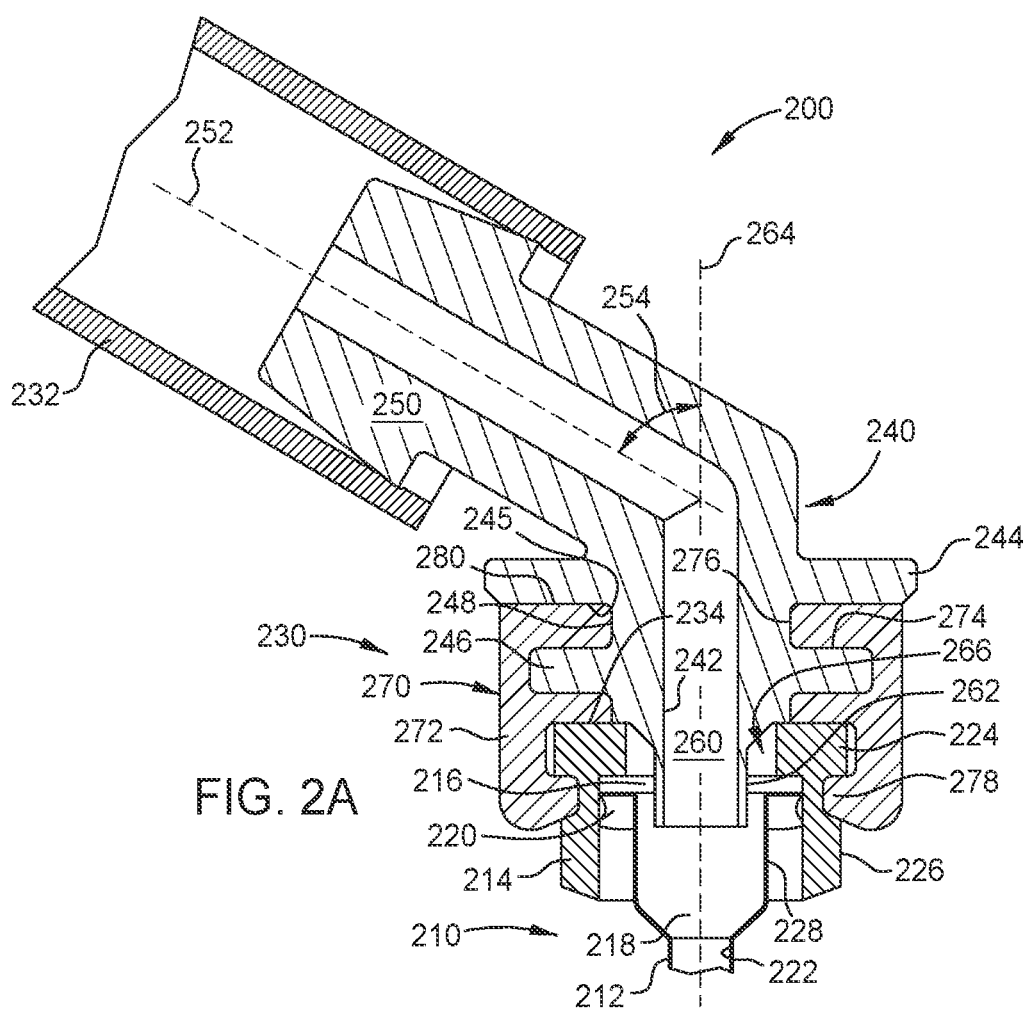
FIG. 2B is a top isometric view of the exemplary infusion cannula of FIG. 2A.
Figure 2B:
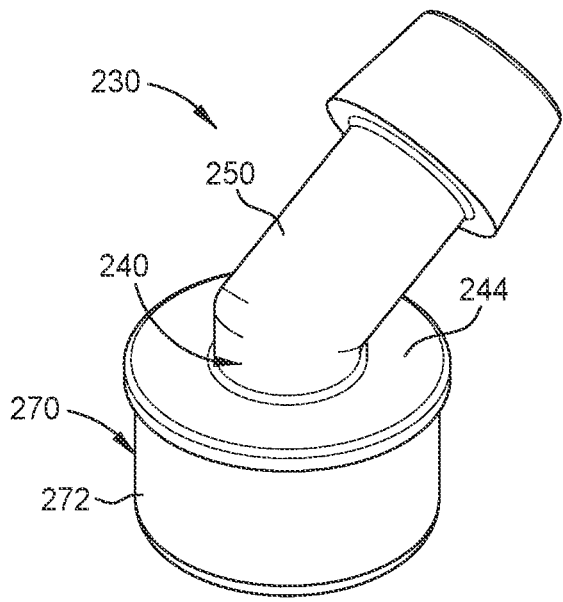
Figure 2C:
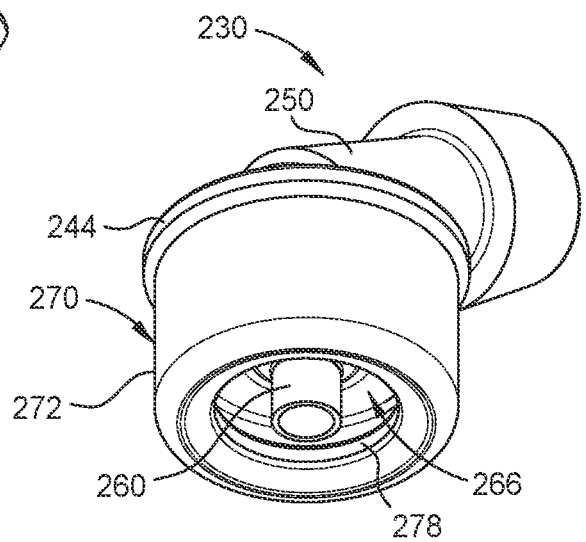
FIG. 2C is a bottom isometric view of the exemplary infusion cannula of FIG. 2A.

As shown in FIG. 2A, the distal end of the infusion cannula 230 radially surrounds and couples to the hub 214 of the valved cannula 210. FIGS. 2B-2C are top and bottom isometric views, respectively, of the infusion cannula 230 of FIG. 2A. FIGS. 2A-2C are, therefore, described together herein for clarity. The infusion cannula 230 generally includes a tubular body 240 with a tubular inlet 250 at a proximal end, a tubular outlet 260 at a distal end, and a retention piece 270 extending from and/or coupled to an outer surface 248 of the distal end of the tubular body 240. In certain embodiments, the tubular inlet 250 is configured to be coupled to an inlet tube 232. The inlet tube 232 is configured to supply fluid, such as liquid or gas (e.g., BSS), to the tubular inlet 250 of the infusion cannula 230 for subsequent infusion into the eye. In the example of FIG. 2A, the tubular inlet 250 has a luer connection at the proximal end to attach the inlet tube 232 thereto. In certain embodiments, an inner diameter for fluid flow through the tubular inlet 250 is tapered such that a first inner diameter at the proximal end of the tubular inlet 250 is greater than a second inner diameter at a distal end of the tubular inlet 250, which is located at angle 254. In such embodiments, the inner diameter of the remainder of the tubular body 240 is about equal to the second inner diameter which is the same as FIG. 2A. In certain embodiments, the tubular inlet 250 and the inner diameter for fluid flow through the tubular inlet 250 are enlarged relative to the remaining fluid flow path through the tubular body 240.

The tubular outlet 260 is located at the distal end of the tubular body 240 and is configured to extend through the valve septum 216 of the hub 214 of the valved cannula 210 as shown in FIG. 2A. A diameter of outer surface 262 and length of the tubular outlet 260 are sized to fit through the valve septum 216. Because the tubular outlet 260 extends through the valve septum 216, which may be referred to as a "valve defeat" geometry, fluid supplied through the tubular outlet 260 is able to pass through the valve septum 216 and into the cannula portion 212 of the valved cannula 210 for subsequent infusion into the eye. As shown in FIG. 2A, the tubular outlet 260 is aligned with a first longitudinal axis 264.

The tubular body 240 is integrally formed, for example by injection molding. In certain embodiments, the tubular body 240 comprises at least one of a thermoplastic elastomer or a rigid polymer such as polypropylene. A continuous flow path is formed between the tubular inlet 250 and tubular outlet 260 of the tubular body 240. In certain embodiments, a minimum inner diameter 242 of the flow path is greater than the inner diameter 222 of the cannula portion 212 of the valved cannula 210. For example, the minimum inner diameter 242 may be greater than the inner diameter 222 of a 23 Gauge valved cannula. For example, the minimum inner diameter 242 may be about 0.02 inches or greater, such as about 0.02 inches to about 0.03 inches, such as about 0.025 inches. The relatively greater minimum inner diameter 242 of the infusion cannula 230 compared to inner diameter 222 of the valved cannula 210 is configured to reduce overall flow resistance and pressure drop through the infusion cannula 230 compared to the valved cannula 210 and compared to existing infusion cannula designs.

In certain embodiments, a lower source pressure may be used to maintain a given flow rate with infusion cannula embodiments disclosed herein. In certain embodiments, source pressure may be reduced proportional to the decrease in flow resistance. In certain embodiments, flow rate may be increased at a given source pressure with infusion cannula embodiments disclosed herein. In certain embodiments, at 120 mmHg (millimeters of mercury) source pressure, the decrease in pressure drop may be about 10% or greater, such as about 10% to about 40%, such as about 20%, such as about 35%, depending on gauge size and compared to existing infusion cannula designs. In certain embodiments, at 120 mmHg source pressure, the increase in flow rate may be about 1% or greater, such as about 1% to about 30%, such as about 1% to about 10%, such as about 2%, such as about 10% to about 30%, such as about 20%, depending on gauge size and compared to existing infusion cannula designs.

As shown in FIG. 2A, the tubular inlet 250 is angled in relation to the first longitudinal axis 264 of the tubular outlet 260. In certain embodiments, an angle 254 measured between the first longitudinal axis 264 of the tubular outlet 260 and a second longitudinal axis 252 of the tubular inlet 250 is greater than about 15°, such as about 15° to about 90°, such as about 15° to about 45°, such as about 30° to about 60°, such as about 45° to about 75°, such as about 60° to about 90°, such as about 30° to about 45°, such as about 60°. Although any angle between the first and second longitudinal axes 264, 252 is possible and disclosure of examples thereof are not intended to be limiting beyond the scope of the claims that follow, it is contemplated that angles below about 15° may not adequately help with routing of the inlet tube 232 to remove the need for creating a service loop or to reduce the profile thereof, while angles above about 90° may cause the inlet tube 232 to interfere with the eye or anatomical structures surrounding the eye. Angles within the disclosed range may also limit undesirable kinking of the inlet tube 232 which interferes with flow and pressure communication therethrough.

The tubular body 240 includes a flange 244 extending from an outer surface 248 of the tubular body 240 in a direction orthogonal to the first longitudinal axis 264 of the tubular outlet 260. It is contemplated that the flange 244 may add strength and/or rigidity to the tubular body and may help stabilize the connection between the infusion cannula 230 and the hub 214 by helping transfer force from the retention piece 270 to the tubular body 240. For example in FIG. 2A, a distal face 245 of the flange 244 contacts a proximal end 280 of the retention piece 270 and load may be transferred across an interface formed therebetween. In the embodiments illustrated in FIG. 2A, an annular disc 246 extends from the outer surface 248 of the tubular body 240 in a direction orthogonal to the first longitudinal axis 264 of the tubular outlet 260. The annular disc 246 is spaced from the flange 244 in a distal direction in relation to the infusion cannula 230 and is configured to provide a structure for coupling the tubular body 240 to the retention piece 270.

As shown in FIG. 2A, the retention piece 270 comprises an annular body 272 surrounding the tubular body 240, including the tubular outlet 260, of the infusion cannula 230. An annular recess 274 is formed on an inner surface 276 of the annular body 272. As shown in FIG. 2A, a shape and position of the annular recess 274 is designed to fit with the annular disc 246 in order to couple the retention piece 270 to the tubular body 240. In certain embodiments, the retention piece 270 comprises a soft elastomer material, such as silicone. The soft elastomer provides added flexibility to the annular body 272 to fit around the annular disc 246 during assembly. In certain embodiments, the retention piece 270 is formed by injection molding. In certain embodiments, the retention piece 270 is formed separately from and subsequently coupled together with the tubular body 240 as described above. In some other embodiments, the retention piece 270 is over molded onto the tubular body 240 during fabrication. In certain embodiments, the infusion cannula 230, including the tubular body 240 and the retention piece 270, is translucent to minimize the perceived profile thereof.

The annular body 272 extends from the annular recess 274 in the distal direction in relation to the infusion cannula 230 and surrounds the tubular outlet 260 at the distal end of the infusion cannula 230. An annular space 266 is formed radially between the annular body 272 and the outer surface 262 of the tubular outlet 260 for receiving a proximal end 234 of the hub 214. The annular body 272 is configured to be coupled to the hub 214 as shown in FIG. 2A. In general, the retention piece 270 and the hub 214 have mating locking features which interlock with each other in the assembled position. In operation, through this interlock, the retention piece 270 can be disengaged from the hub 214 and re-attached to the same or a different hub for repeated use.

In certain embodiments, a profile 278 formed on an inner surface of the annular body 272 is configured to form a snap fit with an overhang 224 formed on an outer surface 226 of the hub 214. In certain embodiments, the profile 278 has a shape which is conformal to a corresponding shape of the outer surface 226 of the hub 214 including the overhang 224. To form the snap fit between the retention piece 270 and the hub 214, the retention piece 270 is pressed onto the hub 214 and into a fully seated position therewith. As the retention piece 270 is pressed onto the hub 214, the profile 278 flexes outward to fit around the overhang 224 and retracts inward to grip the overhang 224 when the valved cannula assembly 200 is assembled. To release the snap fit between the retention piece 230 and the hub 214, the retention piece 270 is pulled away from the hub 214 and out of the fully seated position therewith. As a result of different-sized valved cannulas having the same size hub 214 and the retention piece 270 being coupled to the outer surface 226 of the hub 214, the infusion cannula 230 is cross-compatible with different-sized valved cannulas. For example, certain 23 Gauge, 25 Gauge, and 27 Gauge valved cannulas use the same size hub. Therefore, a single infusion cannula 230 may be configured to fit each of the different sizes.

Figure 3:
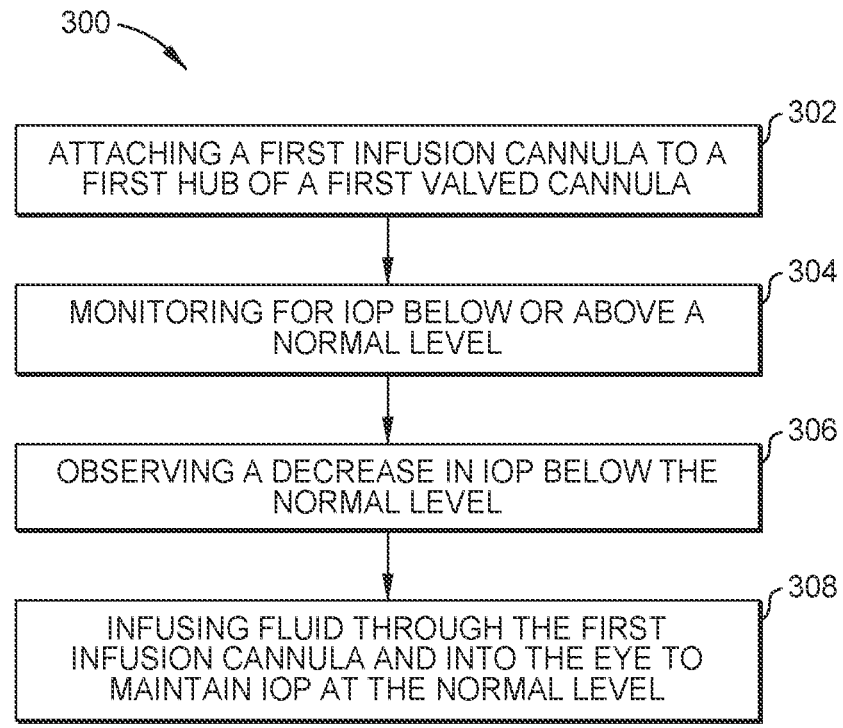
FIG. 3 is a diagram illustrating an exemplary method of using the valved cannula assembly of FIG. 2A for controlling intraocular pressure, in accordance with certain embodiments of the present disclosure.
Figure 4:
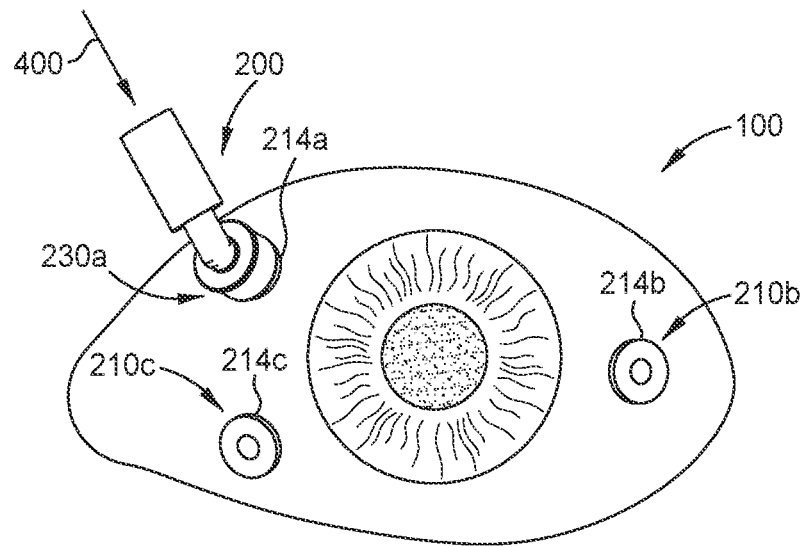
FIG. 4 is a front schematic view of the eye illustrating one stage of the method of FIG. 3, in accordance with certain embodiments of the present disclosure.

FIG. 3 is a diagram illustrating an exemplary method 300 of using the valved cannula assembly 200 of FIG. 2A for controlling IOP during an ophthalmic procedure. At operation 302, a first infusion cannula 230a is attached to a first hub 214a of a first valved cannula as shown in FIG. 4. In certain embodiments, second and third valved cannulas 210b, 210c having respective second and third hubs 214b, 214c remain open for passing instruments therethrough during infusion. At operation 304, IOP is monitored to determine whether IOP is below or above a normal level. At operation 306, a decrease in IOP below the normal level is observed. At operation 308, fluid (e.g., BSS) is infused through the first infusion cannula 230a and into the eye 100 to maintain IOP at the normal level (infusion is shown by arrow 400 in FIG. 4).

Figure 5:
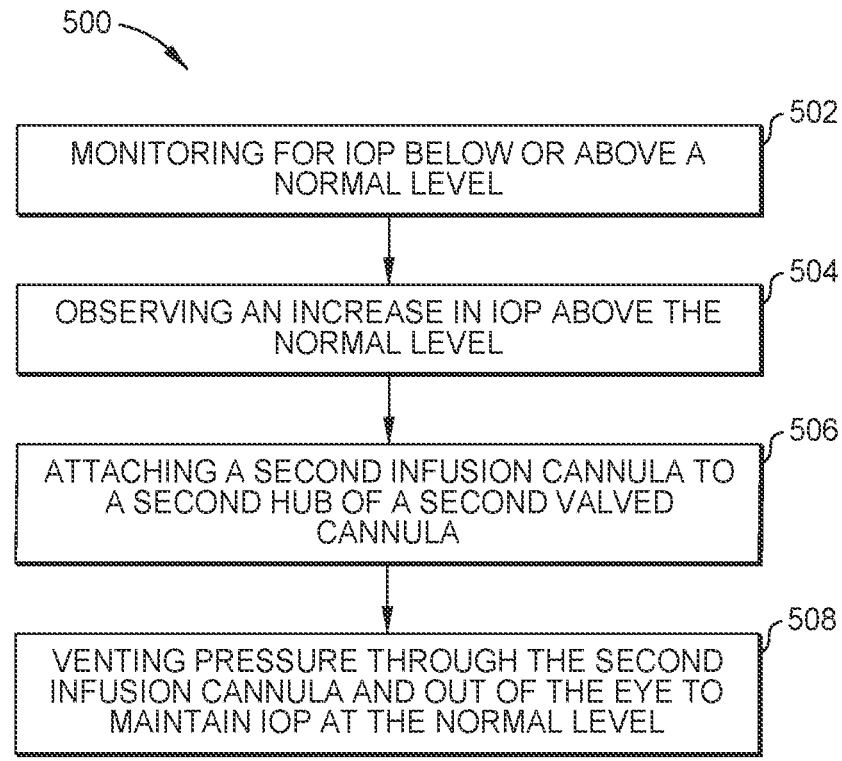
FIG. 5 is a diagram illustrating another exemplary method of using the valved cannula assembly of FIG. 2A for controlling intraocular pressure, in accordance with certain embodiments of the present disclosure.
Figure 6:
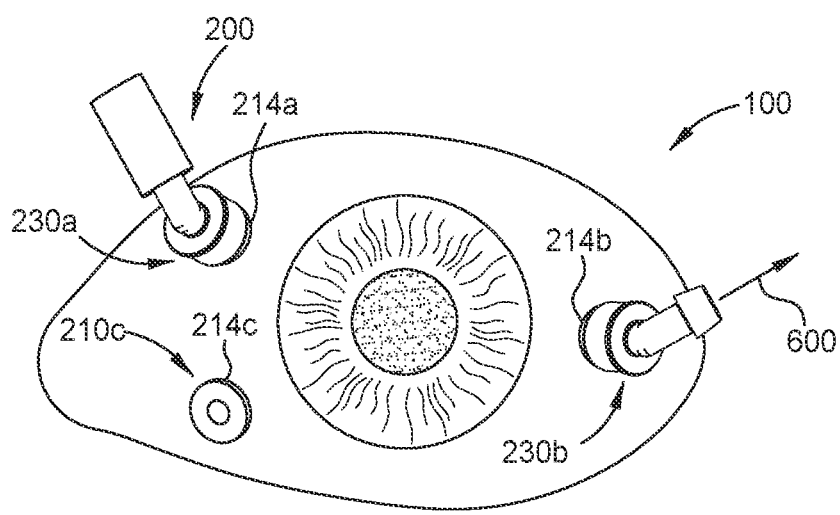
FIG. 6 is a front schematic view of the eye illustrating one stage of the method of FIG. 5, in accordance with certain embodiments of the present disclosure.

FIG. 5 is a diagram illustrating another exemplary method 500 of using the valved cannula assembly 200 of FIG. 2A for controlling IOP during an ophthalmic procedure. At operation 502, IOP is monitored to determine whether IOP is below or above a normal level. At operation 504, an increase in IOP above the normal level is observed. At operation 506, a second infusion cannula 230b is attached to a second hub 214b of a second valved cannula as shown in FIG. 6. In certain embodiments, third valved cannula 210c having third hub 214c remains open for passing instruments therethrough during venting. At operation 508, pressure is vented through the second infusion cannula 230b and out of the eye 100 to maintain IOP at the normal level (venting is shown by arrow 600 in FIG. 6).

Figure 7:
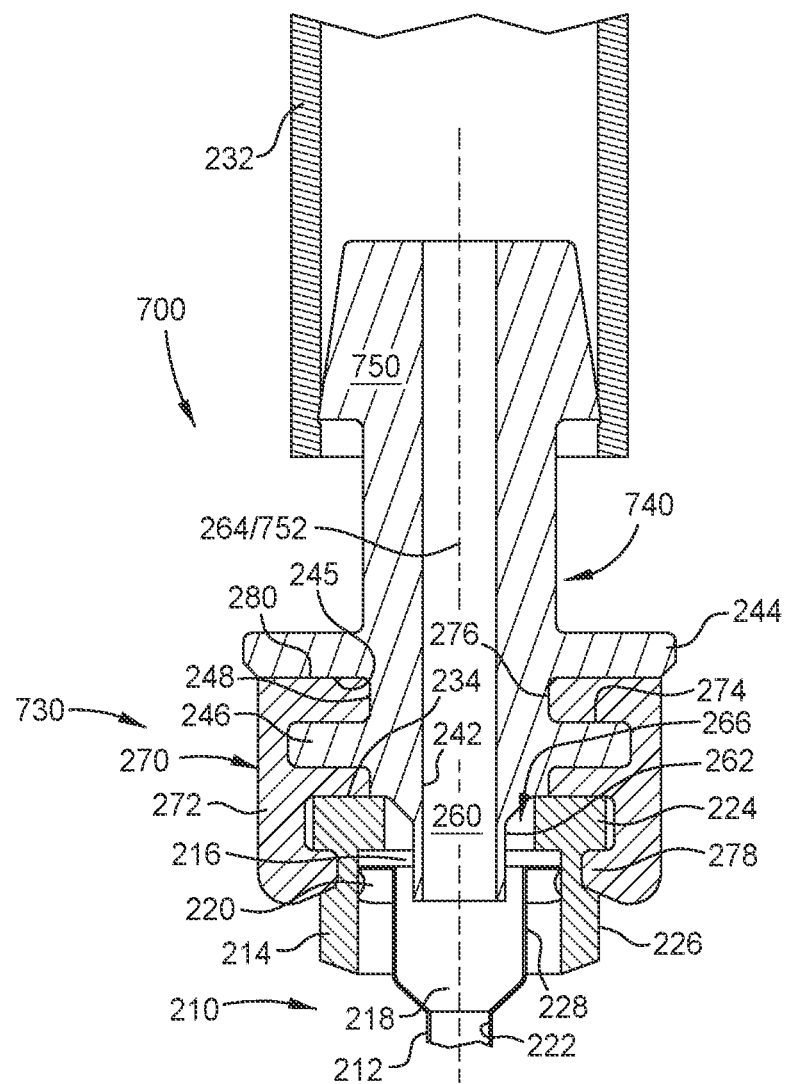
FIG. 7 is a side cross-sectional view of another exemplary infusion cannula with a straight inlet shown assembled with the valved cannula of FIG. 2A.

FIG. 7 is a side cross-sectional view of another exemplary infusion cannula 730 with a straight inlet shown assembled with the valved cannula 210 of FIG. 2A. Referring to FIG. 7, the valved cannula 210 is the same as that shown in FIG. 2A. In certain embodiments, the infusion cannula 730 may be constructed and arranged similar to the infusion cannula 230 of FIG. 2A, and aspects of the description thereof may be incorporated herein without limitation. For example, the tubular outlet 260 and retention piece 270 of the infusion cannula 730 are the same as that shown in FIG. 2A. However, in contrast to the angled inlet of the infusion cannula 230 of FIG. 2A, the infusion cannula 730 has a straight inlet as shown in FIG. 7. In other words, a second longitudinal axis 752 of the tubular inlet 750 is at least substantially aligned with the first longitudinal axis 264 of the tubular outlet 260. The straight inlet of the infusion cannula 730 may be beneficial for use in certain locations on the eye or certain orientations of the infusion cannula when use of the angled inlet would cause the inlet tube 232 to interfere with the eye, anatomical structures surrounding the eye or other aspects of the procedure.

Figure 8:
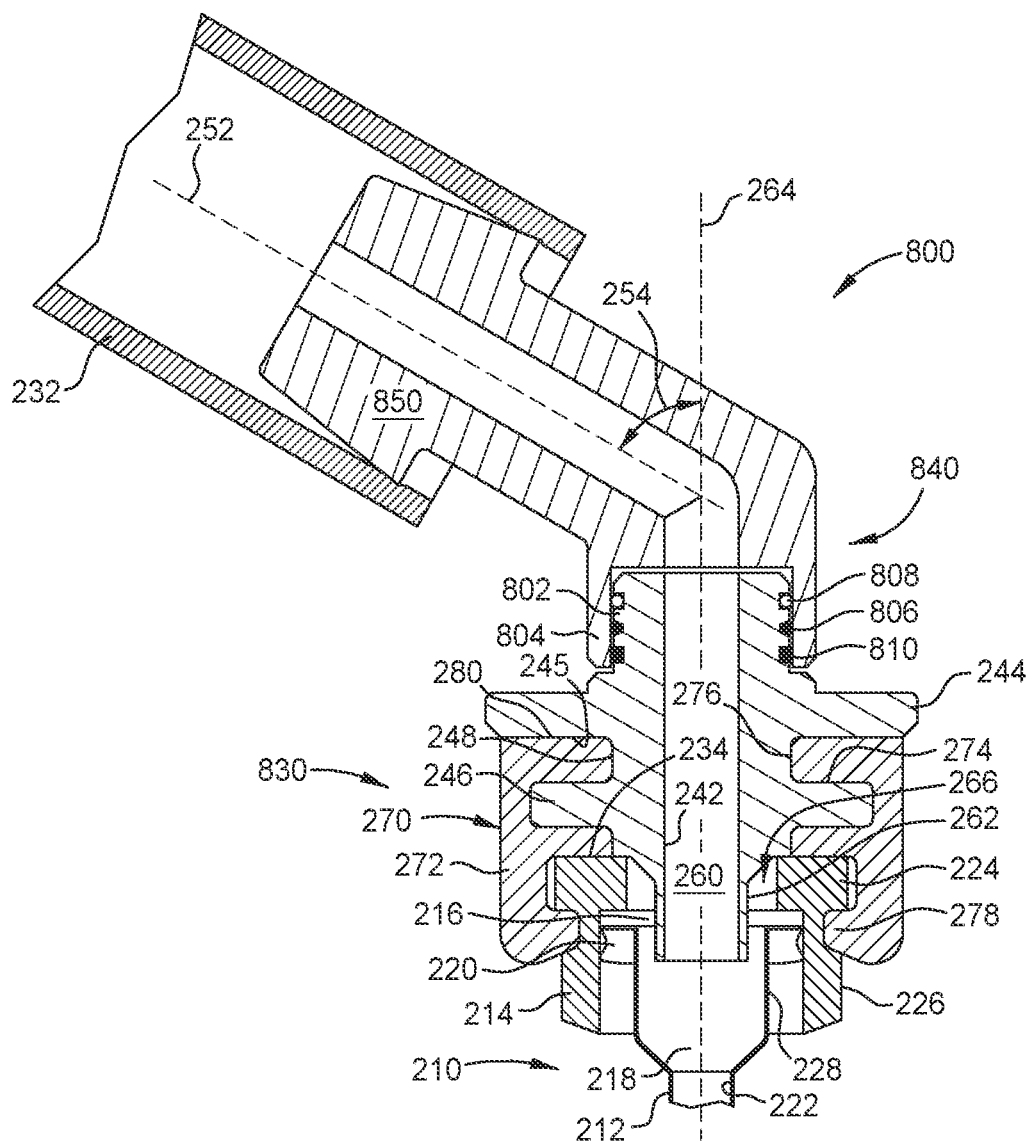
FIG. 8 is a side cross-sectional view of yet another exemplary infusion cannula with a swiveling inlet shown assembled with the valved cannula of FIG. 2A.

FIG. 8 is a side cross-sectional view of yet another exemplary infusion cannula 830 with a swiveling inlet shown assembled with the valved cannula 210 of FIG. 2A. Referring to FIG. 8, the valved cannula 210 is the same as that shown in FIG. 2A. In certain embodiments, the infusion cannula 830 may be constructed and arranged similar to the infusion cannula 230 of FIG. 2A, and aspects of the description thereof may be incorporated herein without limitation. For example, the tubular outlet 260 and retention piece 270 of the infusion cannula 830 are the same as that shown in FIG. 2A. However, in contrast to the infusion cannula 230 of FIG. 2A in which the tubular body 240 is integrally formed, the tubular inlet 850 is configured to swivel with respect to the remainder of the tubular body 840 as shown in FIG. 8. In certain embodiments, the tubular inlet 850 is configured to swivel in relation to the tubular outlet 260 about the first longitudinal axis 264 of the tubular outlet 260. The swiveling inlet of the infusion cannula 830 may be beneficial for use in certain locations on the eye or certain orientations of the infusion cannula when having a fixed orientation of the inlet would cause the inlet tube 232 to interfere with the eye, anatomical structures surrounding the eye or other aspects of the procedure. In such circumstances, the tubular inlet 850 may be swiveled to route the inlet tube 232 to a more convenient location.

Referring to FIG. 8, a stem portion 802 of the tubular body 840 is disposed within and rotatably coupled to a female fitting 804 formed at a distal end of the tubular inlet 850. A plurality of ball bearings 806 are located at an interface between the stem portion 802 and the female fitting 804 to facilitate rotation of the tubular inlet 850 relative to the tubular body 840. One or more seals, such as o-ring seal 808 and ring seal 810, are located at the interface between the stem portion 802 and the female fitting 804 to effect sealing between the stem portion 802 and the female fitting 804. In certain embodiments, the swiveling inlet may be constructed without bearings since rotation of the tubular inlet 850 is only for positioning. In FIG. 8, the tubular inlet 850 only rotates about the first longitudinal axis 264 and therefore has one rotational degree of freedom. However, in some other embodiments, a universal joint may be used, for example between the tubular inlet 850 and the tubular body 840, to allow the tubular inlet 850 to rotate about multiple axes and therefore have two or three rotational degrees of freedom.

FIG. 9A is a side cross-sectional view of yet another exemplary infusion cannula 930 shown assembled with the valved cannula 210 of FIG. 2A. Referring to FIG. 9A, the valved cannula 210 is the same as that shown in FIG. 2A. In certain embodiments, the infusion cannula 930 may be constructed and arranged similar to the infusion cannula 230 of FIG. 2A, and aspects of the description thereof may be incorporated herein without limitation. FIGS. 9B-9C are top and bottom isometric views, respectively, of the infusion cannula 930 of FIG. 9A. FIGS. 9A-9C are, therefore, described together herein for clarity.

In contrast to the infusion cannula 230 of FIG. 2A, the tubular body 940 and the retention piece 970 are integrally formed as a single piece. In certain embodiments, the infusion cannula 930 is formed by injection molding. In certain embodiments, the infusion cannula 930 comprises at least one of a thermoplastic elastomer or a rigid polymer such as polypropylene. In contrast to the infusion cannula 230 of FIG. 2A where the flange 244 contacts the retention piece 270, in FIG. 9A a distal face 945 of the flange 944 is open to the annular space 966 which is formed radially between the annular body 972 and the outer surface 962 of the tubular outlet 960. Therefore, when the valved cannula assembly 900 is fully assembled, the distal face 945 of the flange 944 contacts the proximal end 234 of the hub 214 as shown in FIG. 9A. The infusion cannula 930 has a lower profile (e.g., defined in terms of the distance the infusion cannula extends away from the front of the eye) compared to some other embodiments disclosed herein, such as the infusion cannula 230 for example. It is contemplated that the lower profile of the infusion cannula 930 may be beneficial for reducing visual and physical obstructions during surgical procedures.

The infusion cannula 930 is configured to be coupled to the hub 214 as shown in FIG. 9A. In certain embodiments, a profile 978 formed on an inner surface of the annular body 972 is configured to form a snap fit with an overhang 224 formed on an outer surface 226 of the hub 214. In contrast to the infusion cannula 230 of FIG. 2A, one or more windows 974 are formed radially through the annular body 972. The windows 974 provide added flexibility to the annular body 972 to fit around the overhang 224 during assembly. The windows 974 have a height h1 sized to receive a corresponding portion of the overhang 224 therein to help secure the infusion cannula 930 to the hub 214 when the valved cannula assembly 900 is fully assembled. A slit 982 is formed in the annular body 972 as shown in FIG. 9A and FIG. 9C. The slit 982 provides a better snap fit by allowing the annular body 972 to expand as the annular body 972 is pressed onto the hub 214 and contract as the annular body 972 moves into the fully seated position with the hub 214.

Infusion cannula embodiments disclosed herein are useful for controlling IOP during ophthalmic surgery through infusion/venting of fluids to/from the eye. Certain embodiments provide an improved infusion cannula having an angled inlet which helps with routing of inlet tubing to remove the need for creating a service loop. The angled inlet reduces visual and physical obstructions and reduces surgical time by removing a procedure step. The angled inlet also limits undesirable kinking of the inlet tube which interferes with flow and pressure communication therethrough. Certain embodiments provide an improved infusion cannula which is configured to be coupled to an outer surface of a valved cannula hub. Coupling of the infusion cannula to the outer surface of the hub enables the infusion cannula to be cross-compatible with different-sized valved cannulas expanding potential use cases for the infusion cannula. Certain embodiments provide an improved infusion cannula which has an inner diameter for fluid flow which is greater than a corresponding inner diameter of a compatible valved cannula hub. The improved infusion cannula is configured to reduce overall flow resistance and pressure drop through the infusion cannula which lowers the pressure needed to maintain a given fluid flow rate or, stated another way, increases flow rate at a given source pressure. Certain embodiments provide an improved infusion cannula with a straight inlet as an alternative to the angled inlet. Certain embodiments provide an improved infusion cannula with a swiveling inlet which may be swiveled to route inlet tubing to a more convenient location. Certain embodiments provide an improved infusion cannula having a lower profile for reducing visual and physical obstructions during surgical procedures.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. An infusion cannula, comprising:
   a tubular body with a tubular inlet located at a proximal end of the tubular body and a tubular outlet located at a distal end of the tubular body, the tubular outlet aligned with a first longitudinal axis and configured to extend through a septum of a valved cannula hub; and
   a retention piece extending from or coupled to the tubular body, the retention piece having an annular body surrounding the tubular body at the distal end of the tubular body and configured to be coupled to the valved cannula hub, wherein an inner surface of the annular body has a profile configured to form a snap fit with an overhang formed along an outer surface of the valved cannula hub;
   wherein a slit is formed in the annular body to allow the annular body to expand as the annular body is pressed onto the valved cannula hub and contract as the annular body moves into a fully seated position with the valved cannula hub.

2. The infusion cannula of claim 1, wherein the tubular inlet is angled in relation to the first longitudinal axis of the tubular outlet.

3. The infusion cannula of claim 2, wherein an angle measured between the first longitudinal axis of the tubular outlet and a second longitudinal axis of the tubular inlet is about 15° to about 90°.

4. The infusion cannula of claim 1, wherein a second longitudinal axis of the tubular inlet is at least substantially aligned with the first longitudinal axis of the tubular outlet.

5. The infusion cannula of claim 1, wherein the tubular body is integrally formed, and wherein the retention piece comprises a soft elastomer formed separately from and subsequently coupled together with the tubular body.

6. The infusion cannula of claim 1, wherein the tubular body and retention piece are integrally formed and comprise at least one of a thermoplastic elastomer or a rigid polymer.

7. The infusion cannula of claim 1, wherein the tubular inlet is configured to swivel in relation to the tubular outlet about the first longitudinal axis of the tubular outlet.

8. The infusion cannula of claim 1, wherein the retention piece is configured to fit a plurality of different-sized valved cannulas including at least 23 Gauge, 25 Gauge, and 27 Gauge valved cannulas.

9. The infusion cannula of claim 1, wherein an inner diameter of the tubular outlet is greater than an inner diameter of the valved cannula, and wherein the greater inner diameter of the tubular outlet is configured to reduce overall flow resistance through the infusion cannula compared to the valved cannula.

10. The infusion cannula of claim 1, wherein to form the snap fit between the retention piece and the valved cannula hub, the retention piece is pressed onto the valved cannula hub and into a fully seated position therewith, and wherein to release the snap fit between the retention piece and the valved cannula hub, the retention piece is pulled away from the valved cannula hub and out of the fully seated position therewith.

11. The infusion cannula of claim 1, wherein the tubular body further comprises an annular disc extending from the outer surface thereof in a direction orthogonal to the first longitudinal axis of the tubular outlet, and wherein an inner surface of the annular body of the retention piece comprises an annular recess fitting the annular disc to couple the retention piece to the tubular body.

12. The infusion cannula of claim 1, wherein the tubular body further comprises a flange extending from an outer surface thereof in a direction orthogonal to the first longitudinal axis of the tubular outlet, and wherein the flange helps transfer force from the retention piece to the tubular body.

13. The infusion cannula of claim 12, wherein a proximal end of the retention piece contacts a distal face of the flange.

14. The infusion cannula of claim 1, wherein an annular space is formed radially between the annular body and an outer surface of the tubular outlet for receiving a proximal end of the valved cannula hub.

\* \* \* \* \*